(12) United States Patent     (10) Patent No.: US 8,293,926 B2
Yasuoka et al.     (45) Date of Patent: Oct. 23, 2012

(54) METHOD OF PRODUCING OPTICALLY ACTIVE 4-AMINO-3-SUBSTITUTED PHENYLBUTANOIC ACID

(75) Inventors: Junichi Yasuoka, Kobe (JP); Shoji Fukuyo, Nishinomiya (JP); Tetsuya Ikemoto, Toyonaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 557 days.

(21) Appl. No.: 12/086,056

(22) PCT Filed: Dec. 8, 2006

(86) PCT No.: PCT/JP2006/325001
§ 371 (c)(1),
(2), (4) Date: Jun. 5, 2008

(87) PCT Pub. No.: WO2007/066828
PCT Pub. Date: Jun. 14, 2007

(65) Prior Publication Data
US 2009/0137819 A1     May 28, 2009

(30) Foreign Application Priority Data
Dec. 9, 2005    (JP) ................................ 2005-356795
May 15, 2006    (JP) ................................ 2006-135636

(51) Int. Cl.
*C07D 207/273*    (2006.01)
*C07C 229/34*    (2006.01)

(52) U.S. Cl. ....................................... 548/540; 562/443
(58) Field of Classification Search .................. 548/540, 548/532; 562/443
See application file for complete search history.

(56) References Cited

U.S. PATENT DOCUMENTS
2005/0101787 A1    5/2005    Watanabe et al.
(Continued)

FOREIGN PATENT DOCUMENTS
EP    1 512 678 A1    3/2005
(Continued)

OTHER PUBLICATIONS

Okino et al. J. Am. Chem. Soc. 2005, 127, Supplemental Information (pp. S1-S21).*

(Continued)

*Primary Examiner* — Jason M Nolan
(74) *Attorney, Agent, or Firm* — Birch, Stewart, Kolasch & Birch, LLP

(57) ABSTRACT

The present invention provides a method of producing a compound (IIa) or a compound (IIb), provides a method of producing a compound (IIIa) or a compound (IIIb), provides a method of producing a compound (Va) or its salt or a compound (Vb) or its salt, provides a method of producing a compound (IIIa) or a compound (IIIb), further, provides a method of producing a compound (Va) or its salt or a compound (Vb) or its salt including these production methods.

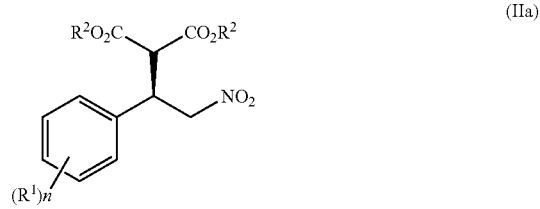

(IIa)

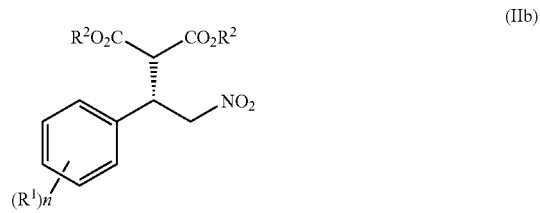

(IIb)

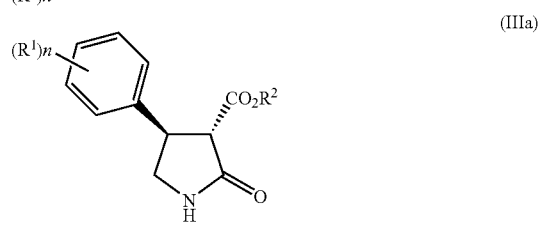

(IIIa)

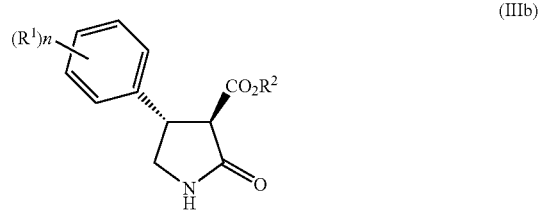

(IIIb)

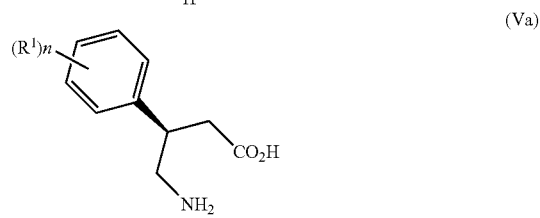

(Va)

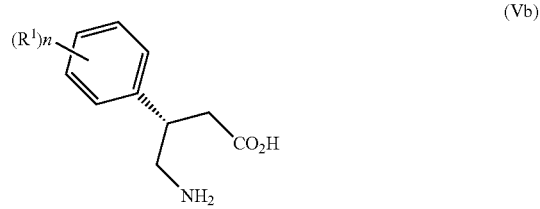

(Vb)

39 Claims, No Drawings

U.S. PATENT DOCUMENTS

2008/0154036 A1    6/2008    Terada et al.

FOREIGN PATENT DOCUMENTS

| JP | 45-16632 B | 6/1970 |
| JP | 57-40446 A | 3/1982 |
| JP | 4-193850 A | 7/1992 |
| JP | 2005-187446 A | 7/2005 |
| WO | WO-2005/077908 A1 | 8/2005 |

OTHER PUBLICATIONS

English translation of International Preliminary Report on Patentability and Written Opinion of the International Searching Authority (Forms PCT/IB/338, PCT/IB/373 and PCT/ISA/237) issued on Feb. 18, 2010 in PCT/JP2006/325001.

Okino, Tomotaka et al., Journal of the American Chemical Society, 2005, 127 (1), pp. 119-125.

Barnes et al., "Development of a Catalytic Enantioselective Conjugate Addition of 1,3-Dicarbonyl Compounds to Nitroalkenes for the Synthesis of Endothelin-A Antagonist ABT-546. Scope, Mechanism, and Further Application to . . . ," J. Am. Chem. Soc., vol. 124, No. 44, pp. 13097-13105, 2002.

Evans et al., "NI(II)-Bis[(R,R)-N,N-dibenzylcyclohexane-1,2-diamine]Br2 Catalyzed Enantioselective Michael Additions of 1,3-Dicarbonyl Compounds to Conjugated Nitroalkenes," J. Am. Chem. Soc., vol. 127, No. 28, pp. 9958-9959, 2005.

Li et al., "Highly Enantioselective Conjugate Addition of Malonate and β-Ketoester to Nitroalkenes: Asymmetric C-C Bond Formation with New Bifunctional Organic Catalysts Based on Cinchona Alkaloids," J. Am. Chem. Soc., vol. 126, No. 32, pp. 9906-9907, 2004.

Okino et al., "Enantio- and Diastereoselective Michael Reaction of 1,3-Dicarbonyl Compounds to Nitroolefins Catalyzed by a Bifunctional Thiourea," J. Am. Chem. Soc. vol. 127, No. 1, pp. 119-125, 2005.

Watanabe et al., "Catalytic Enantioselective Michael Addition of 1,3-Dicarbonyl Compounds to Nitroalkenes Catalyzed by Well-Defined Chiral Ru Amido Complexes," J. Am. Chem. Soc., vol. 126, No. 36, pp. 11148-11149, 2004.

* cited by examiner

US 8,293,926 B2

METHOD OF PRODUCING OPTICALLY ACTIVE 4-AMINO-3-SUBSTITUTED PHENYLBUTANOIC ACID

TECHNICAL FIELD

The present invention relates to a method of producing an optically active 4-amino-3-substituted phenylbutanoic acid useful as medicine or its salt, and a method producing a compound which is useful as a synthesis intermediate thereof.

BACKGROUND ART (R)-4-amino-3-(4-chlorophenyl)butanoic acid ((R)-(−)-baclofen) is a compound which is useful as a reflux esophagitis remedy or antispasmodic. There are known several methods for synthesizing this compound and, for example, Journal of the American Chemical Society, 2005, vol. 127, p. 119-125 (hereinafter, described as non-patent document 1 in some cases) discloses the following method as a method of efficiently synthesizing the compound.

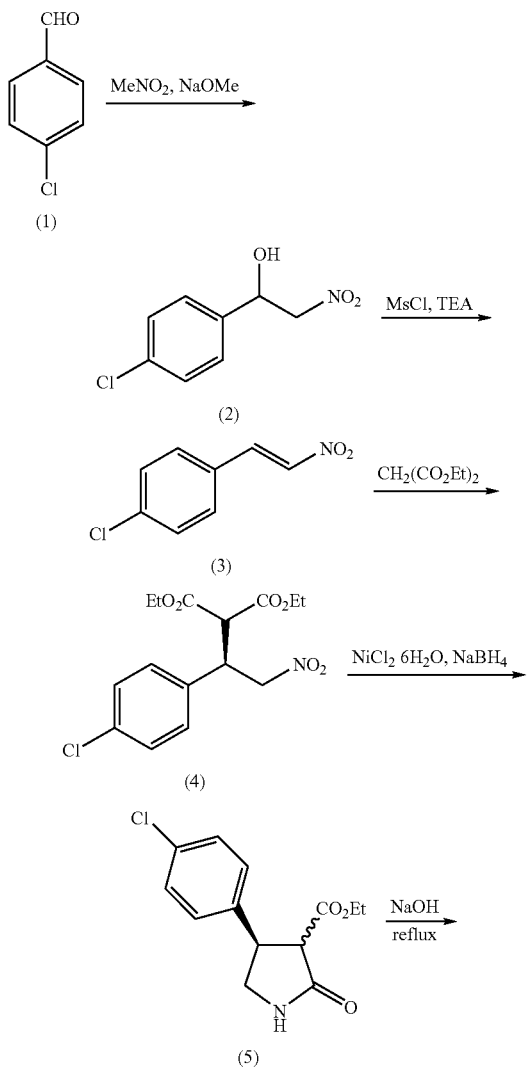

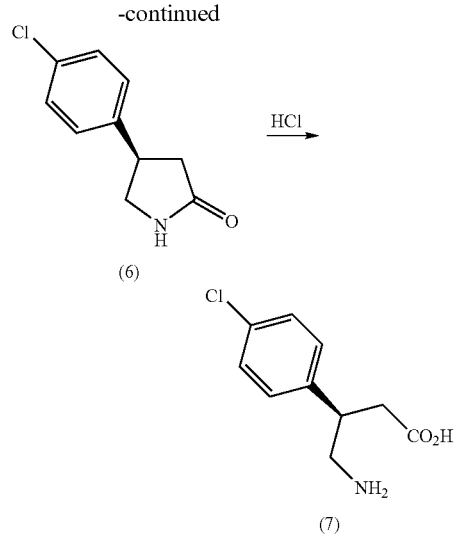

Further, Journal of the American Chemical Society, 2005, vol. 127, p. 9958-9959, Journal of the American Chemical Society, 2004, vol. 126, p. 11148-11149 and Journal of the American Chemical Society, 2004, vol. 126, p. 9906-9907 (hereinafter, described as non-patent document 2, non-patent document 3 and non-patent document 4, respectively, in some cases) disclose production of optically active 2-(1-substituted phenyl-2-nitroethyl)malonic acid diesters typified by diethyl (R)-2-(1-(4-chlorophenyl)-2-nitroethyl)malonate (4) by asymmetric Michael addition of a malonic acid diester to β-nitrostyrenes typified by 4-chloro-β-nitrostyrene (3) using various asymmetric catalysts.

These β-nitrostyrenes and 2-(1-substituted phenyl-2-nitroethyl)malonic acid diesters are dangerous compounds having a fear of explosion because of a nitro group in them. Particularly, β-nitrostyrenes are compounds having a high possibility of explosion since they have a double bond conjugating a nitro group. Therefore, drying these compounds isolated is problematical in point of safety, and accompanied by a danger particularly in production on industrial scale.

Journal of the American Chemical Society, 2002, vol. 124, p. 13097-13105 (hereinafter, described as non-patent document 5 in some cases) discloses a method of producing β-nitrostyrenes, and here, benzaldehydes are reacted with ammonium acetate and nitromethane in acetic acid, then, the deposited crystal is filtrated, washed with water and dried, to obtain β-nitrostyrenes. This method obtains β-nitrostyrenes directly from benzaldehydes, thus, this method shows a shorter process as compared with a method of obtaining 4-chloro-□-nitrostyrene (3) from 4-chlorobenzaldehyde (1) via 4-chloro-α-nitromethylbenzyl alcohol (2) as in the method of the non-patent document 1, and since solvent extraction and the like are not included, this method is an industrially advantageous method. However, in this method, the resultant crystal of β-nitrostyrenes is one finally water-washed, namely, the resultant crystal contains a considerable amount of water, and it is necessary to dry this crystal sufficiently before being subjected to the subsequent process. In this case, however, there is a high danger of explosion and the like as described above, and particularly in production on industrial scale, its safety problem possibly generates a non-applicable disturbance.

In the non-patent document 1, non-patent document 2, non-patent document 3, non-patent document 4 and patent document 1, 2-(1-substituted phenyl-2-nitroethyl)malonic acid diesters are isolated as crystal and dried, however, drying of this compound also inevitably produces a safety problem because of the reason described above.

JPS45-16692B (hereinafter, described as patent document 2 in some cases) discloses a method in which 4-substituted phenyl-2-oxopyrrolidine-3-carboxylic acid esters typified by 4-(4-chlorophenyl)-2-oxopyrrolidine-3-carboxylate ethyl (5) are added to a mineral acid such as hydrochloric acid and the like and the mixture are heated under reflux, to obtain 4-amino-3-substituted phenylbutanoic acids typified by 4-amino-3-(4-chlorophenyl)butanoic acid (7). This method is an industrially advantageous method due to fewer processes since this method is carried out not via 4-substituted phenylpyrrolidin-2-ones typified by 4-(4-chlorophenyl)-pyrrolidin-2-one (6) as in the non-patent document 1. In this method, carbon dioxide is generated, and in the method of adding 4-substituted phenyl-2-oxopyrrolidine-3-carboxylic acid esters as they are to a mineral acid as in the patent document 2, control of carbon dioxide to be generated is difficult, and in some cases, there is a possibility of generation of carbon dioxide at one time, leading to a strict problem in production on industrial scale.

DISCLOSURE OF THE INVENTION

The present invention has an object of providing a method of producing optically active 4-amino-3-substituted phenylbutanoic acids typified by (R)-4-amino-3-(4-chlorophenyl)butanoic acid useful as medicine by a method which solves the problems in the conventional production methods and which is safe, efficient and advantageous on industrial scale, and a method of producing an intermediate in this method.

The present inventors have investigated to solve the above-described problems, resultantly leading to completion of the present invention.

That is, the present invention includes the following items.

<1> A method comprising dissolving or dispersing a hydrate crystal of a compound of the formula (I):

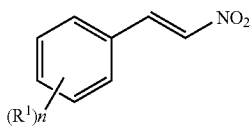

(I)

(wherein, n represents an integer of 0 to 3, $R^1$ represents a halogen atom, alkyl group, alkoxy group, haloalkyl group and cycloalkyloxy group, when n is 2 or 3, $R^1$s may be the same or different, or when n is 2 or 3, two $R^1$s together form an alkylenedioxy group) (hereinafter, described as compound (I) in some cases)

in a solvent, subjecting the solution or dispersion to liquid-separation, to concentration under reduced pressure, or to liquid-separation and concentration under reduced pressure, and reacting the compound of the formula (I) with a compound of the formula (I'):

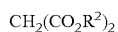

(wherein, $R^2$ represents an alkyl group.) (hereinafter, described as compound (I') in some cases)

in the presence of an asymmetric catalyst, to produce a compound of the formula (IIa):

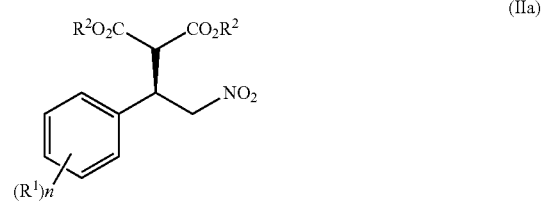

(IIa)

(wherein, $R^1$, $R^2$ and n have the same meanings as described above.) (hereinafter, described as compound (IIa) in some cases) or a compound of the formula (IIb):

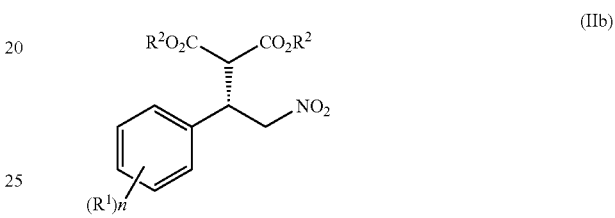

(IIb)

(wherein, $R^1$, $R^2$ and n have the same meanings as described above.) (hereinafter, described as compound (IIb) in some cases).

<2> The method according to <1>, wherein the hydrate crystal contains water in an amount of 0.05 to 3 parts by weight with respect to 1 part by weight of the compound (I).

<3> The method according to <1> or <2>, wherein the compound (I) is produced by reacting a compound of the formula (Ia):

(Ia)

(wherein, $R^1$ and n have the same meanings as described above.) (hereinafter, described as compound (Ia) in some cases) with nitromethane and ammonium acetate in acetic acid.

<4> The method according to any one of <1> to <3>, wherein the solvent for dissolving or dispersing the hydrated crystal of the compound (I) is an aromatic hydrocarbon.

<5> The method according to any one of <1> to <4>, wherein n is 1.

<6> The method according to <5>, wherein $R^1$ is situated at the 4-position of a benzene ring.

<7> The method according to any one of <1> to <4>, wherein n is 1, and $R^1$ is a chlorine atom situated at the 4-position of a benzene ring.

<8> The method according to any one of <1> to <7>, wherein the asymmetric catalyst is 1-(3,5-bis(trifluoromethyl)phenyl)-3-((1R,2R)-2-(dimethylamino)cyclohexyl)thiourea, 1-(3,5-bis(trifluoromethyl)phenyl)-3-((1S,2S)-2-(dimethylamino)cyclohexyl)thiourea, nickel(II)bis[(S,S)—N,N'-dibenzylcyclohexane-1,2-diamine]bromide or nickel(II)bis[(R,R)—N,N'-dibenzylcyclohexane-1,2-diamine]bromide.

<9> The method according to <8>, wherein the asymmetric catalyst is nickel(II)bis[(S,S)—N,N'-dibenzylcyclohexane-1,2-diamine]bromide or nickel(II)bis[(R,R)—N,N'-dibenzylcyclohexane-1,2-diamine]bromide.

<10> A method comprising reacting a compound (I) and a compound (I') in the presence of an asymmetric catalyst, and reducing and cyclizing the resultant compound (IIa) or compound (IIb) without isolation in the form of solution or dispersion, to produce a compound of the formula (IIIa):

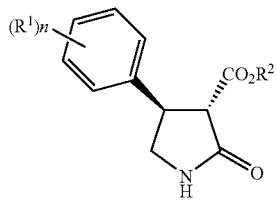

(IIIa)

(wherein, $R^1$, $R^2$ and n have the same meanings as described above.) (hereinafter, described as compound (IIIa) in some cases) or a compound of the formula (IIIb):

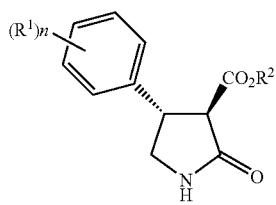

(IIIb)

(wherein, $R^1$, $R^2$ and n have the same meanings as described above.) (hereinafter, described as compound (IIIb) in some cases).

<11> The method according to <10>, wherein the concentration of the compound (IIa) or compound (IIb) is maintained in the range of 10 to 80 wt % from obtaining by the reaction of a compound (I) and a compound (I') to reduction and cyclization.

<12> The method according to <11>, wherein the concentration of the compound (IIa) or compound (IIb) is maintained in the range of 20 to 70 wt %.

<13> The method according to any one of <10> to <12>, wherein the solvent for the compound (IIa) or compound (IIb) in the form of solution or dispersion is an aromatic hydrocarbon.

<14> The method according to any one of <10> to <13>, wherein the reaction of a compound (I) and a compound (I') is carried out after dissolving or dispersing a hydrated crystal of a compound (I) in a solvent, and subjecting the solution or dispersion to liquid-separation, to concentration under reduced pressure, or to liquid-separation and concentration under reduced pressure.

<15> The method according to <14>, wherein the hydrated crystal contains water in an amount of 0.05 to 3 parts by weight with respect to 1 part by weight of the compound (I).

<16> A method of producing a compound of the formula (Va) or its salt or a compound of the formula (Vb) or its salt, comprising a step of reacting a compound (I) and a compound (I') in the presence of a catalyst, and reducing and cyclizing the resultant compound (IIa) or compound (IIb) without isolation in the form of solution or dispersion, to obtain a compound (IIIa) or compound (IIIb);

a step of hydrolyzing and decarboxylating the compound (IIIa) or compound (IIIb) to obtain a compound of the formula (IVa):

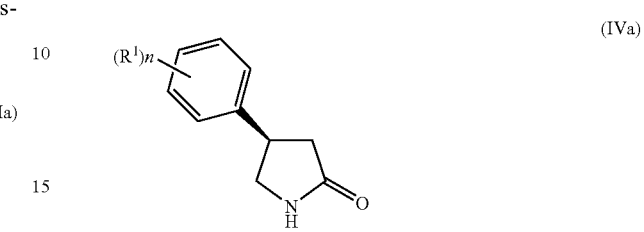

(IVa)

(wherein, $R^1$ and n have the same meanings as described above.) (hereinafter, described as compound (IVa) in some cases) or a compound of the formula (IVb):

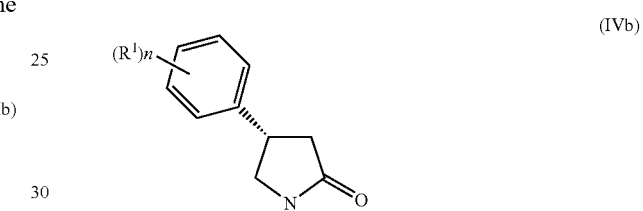

(IVb)

(wherein, $R^1$ and n have the same meanings as described above.) (hereinafter, described as compound (IVb) in some cases); and a step of ring-opening the compound (IVa) or compound (IVb) to obtain a compound of the formula (Va):

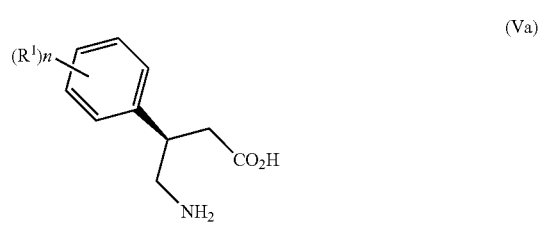

(Va)

(wherein, $R^1$ and n have the same meanings as described above.) (hereinafter, described as compound (Va) in some cases) or its salt or a compound of the formula (Vb):

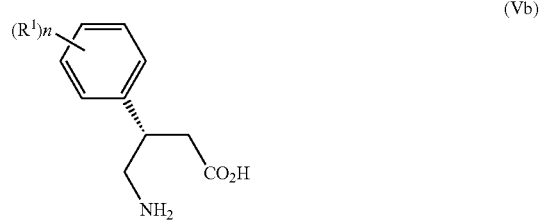

(Vb)

(wherein, $R^1$ and n have the same meanings as described above.) (hereinafter, described as compound (Vb) in some cases) or its salt.

<17> The method according to <16>, wherein the concentration of the compound (IIa) or compound (IIb) is maintained in the range of 10 to 80 wt % from obtaining by the reaction of a compound (I) and a compound (I') to reduction and cyclization.

<18> The method according to <17>, wherein the concentration of the compound (IIa) or compound (IIb) is maintained in the range of 20 to 70 wt %.

<19> The method according to any one of <16> to <18>, wherein the solvent for the compound (IIa) or compound (IIb) in the form of solution or dispersion is an aromatic hydrocarbon.

<20> The method according to any one of <16> to <19>, wherein the reaction of a compound (I) and a compound (I') is carried out after dissolving or dispersing a hydrated crystal of a compound (I) in a solvent, and subjecting the solution or dispersion to liquid-separation, to concentration under reduced pressure, or to liquid-separation and concentration under reduced pressure.

<21> The method according to <20>, wherein the hydrated crystal contains water in an amount of 0.05 to 3 parts by weight with respect to 1 part by weight of the compound (I).

<22> A method comprising dissolving or dispersing a compound (IIIa) or compound (IIIb) in a solvent, and adding the resultant solution or dispersion to an acid, to produce a compound (Va) or its salt or a compound (Vb) or its salt, <23> The method according to <22>, wherein the solvent for dissolving or dispersing a compound (IIIa) or compound (IIIb) is a halogenated aromatic hydrocarbon.

<24> The method according to <22> or <23>, wherein the compound (IIIa) or compound (IIIb) is obtained by reducing and cyclizing a compound (IIa) or compound (IIb).

<25> The method according to <24>, wherein the reduction of a compound (IIa) or compound (IIb) is catalytic hydrogen reduction in the presence of a developed nickel containing iron.

<26> The method according to <25>, wherein the iron content of the developed nickel containing iron is 0.1 to 50 wt %.

<27> The method according to <25> or <26>, wherein the compound (IIa) or compound (IIb) is obtained by reacting a compound (I) and a compound (I') in the presence of an asymmetric catalyst.

<28> The method according to <27>, wherein the reaction of a compound (I) and a compound (I') is carried out after dissolving or dispersing a hydrated crystal of a compound (I) in a solvent, and subjecting the solution or dispersion to liquid-separation, to concentration under reduced pressure, or to liquid-separation and concentration under reduced pressure.

<29> The method according to <22> or <23>, wherein the compound (IIIa) or compound (IIIb) is obtained by reacting a compound (I) and a compound (I') in the presence of an asymmetric catalyst, and reducing and cyclizing the resultant compound (IIa) or compound (IIb) in the form of solution or dispersion without isolation.

<30> The method according to <29>, wherein the reduction of a compound (IIa) or compound (IIb) is catalytic hydrogen reduction in the presence of a developed nickel containing iron.

<31> The method according to <30>, wherein the iron content of the developed nickel containing iron is 0.1 to 50 wt %.

<32> The method according to <29>, wherein the reaction of a compound (I) and a compound (I') is carried out after dissolving or dispersing a hydrated crystal of a compound (I) in a solvent, and subjecting the solution or dispersion to liquid-separation, to concentration under reduced pressure, or to liquid-separation and concentration under reduced pressure, and the reduction of a compound (IIa) or compound (IIb) is catalytic hydrogen reduction in the presence of a developed nickel containing iron.

<33> The method according to any one of <29> to <32>, wherein the concentration of the compound (IIa) or compound (IIb) is maintained in the range of 10 to 80 wt % from obtaining by the reaction of a compound (I) and a compound (I') to reduction and cyclization.

<34> The method according to <33>, wherein the concentration of the compound (IIa) or compound (IIb) is maintained in the range of 20 to 70 wt %.

<35> The method according to any one of <29> to <34>, wherein the solvent for the compound (IIa) or compound (IIb) in the form of solution or dispersion is an aromatic hydrocarbon.

<36> The method according to any one of <29> to <35>, wherein the reaction of a compound (I) and a compound (I') is carried out after dissolving or dispersing a hydrated crystal of a compound (I) in a solvent, and subjecting the solution or dispersion to liquid-separation, to concentration under reduced pressure, or to liquid-separation and concentration under reduced pressure.

<37> The method according to <36>, wherein the hydrated crystal contains water in an amount of 0.05 to 3 parts by weight with respect to 1 part by weight of the compound (I).

<38> A method comprising catalytic hydrogen reduction and cyclization of a compound (IIa) or compound (IIb) in the presence of a developed nickel containing iron, to produce a compound (IIIa) or compound (IIIb).

<39> The method according to <38>, wherein the iron content of the developed nickel containing iron is 0.1 to 50 wt %.

<40> The method according to <38> or <39>, wherein the compound (IIa) or compound (IIb) is obtained by reaction of a compound (I) and a compound (I') in the presence of a catalyst, and the catalytic hydrogen reduction in the presence of a developed nickel containing iron is carried out in the form of solution or dispersion of the compound (IIa) or compound (IIb) without isolation.

<41> The method according to <40>, wherein the concentration of the compound (IIa) or compound (IIb) is maintained in the range of 10 to 80 wt % from obtaining by the reaction of a compound (I) and a compound (I') to reduction and cyclization.

<42> The method according to <41>, wherein the concentration of the compound (IIa) or compound (IIb) is maintained in the range of 20 to 70 wt %.

<43> The method according to any one of <40> to <42>, wherein the solvent for the compound (IIa) or compound (IIb) in the form of solution or dispersion is an aromatic hydrocarbon.

<44> The method according to any one of <40> to <43>, wherein the reaction of a compound (I) and a compound (I') is carried out after dissolving or dispersing a hydrated crystal of a compound (I) in a solvent, and subjecting the solution or dispersion to liquid-separation, to concentration under reduced pressure, or to liquid-separation and concentration under reduced pressure.

<45> The method according to <44>, wherein the hydrated crystal contains water in an amount of 0.05 to 3 parts by weight with respect to 1 part by weight of the compound (I).

<46> A method of producing a compound of the formula (Va) or its salt or a compound of the formula (Vb) or its salt, comprising a step of catalytic hydrogen reduction and cyclization of a compound (IIa) or compound (IIb) in the presence of a developed nickel containing iron, to obtain a compound (IIIa) or compound (IIIb);

a step of hydrolysis and decarboxylation of the compound (IIIa) or compound (IIIb), to obtain a compound (IVa) or compound (IVb); and a step of ring-opening the compound (IVa) or compound (IVb), to obtain a compound (Va) or its salt or a compound (Vb) or its salt.

<47> The method according to <46>, wherein the iron content of the developed nickel containing iron is 0.1 to 50 wt %.

<48> The method according to <46> or <47>, wherein the compound (IIa) or compound (IIb) is obtained by reaction of a compound (I) and a compound (I') in the presence of an asymmetric catalyst.

<49> The method according to <48>, wherein the catalytic hydrogen reduction in the presence of a developed nickel containing iron is carried out in the form of solution or dispersion of the compound (IIa) or compound (IIb) without isolation.

<50> The method according to <49>, wherein the concentration of the compound (IIa) or compound (IIb) is maintained in the range of 10 to 80 wt % from obtaining by the reaction of a compound (I) and a compound (I') to reduction and cyclization.

<51> The method according to <50>, wherein the concentration of the compound (IIa) or compound (IIb) is maintained in the range of 20 to 70 wt %.

<52> The method according to any one of <49> to <51>, wherein the solvent for the compound (IIa) or compound (IIb) in the form of solution or dispersion is an aromatic hydrocarbon.

<53> The method according to any one of <48> to <52>, wherein the reaction of a compound (I) and a compound (I') is carried out after dissolving or dispersing a hydrated crystal of a compound (I) in a solvent, and subjecting the solution or dispersion to liquid-separation, to concentration under reduced pressure, or to liquid-separation and concentration under reduced pressure.

<54> The method according to <53>, wherein the hydrated crystal contains water in an amount of 0.05 to 3 parts by weight with respect to 1 part by weight of the compound (I).

<55> A method of producing a compound of the formula (Va) or its salt, comprising a step of reacting a compound (I) with a compound of the formula (I'):

(wherein, $R^2$ represents an alkyl group).
in the presence of nickel(II)bis[(S,S)—N,N'-dibenzylcyclohexane-1,2-diamine]bromide, to obtain a compound (IIa);

a step of reducing and cyclizing the compound (IIa), to obtain a compound (IIIa); and a step of dissolving or dispersing the compound (IIIa) in a solvent, and adding the resultant solution or dispersion to an acid, to obtain a compound (Va) or its salt.

<56> The method according to any one of <10> to <55>, wherein the compound (I) is produced by reacting a compound (Ia) with nitromethane and ammonium acetate in acetic acid.

<57> The method according to <14>, <15>, <20>, <21>, <32>, <33>, <34>, <35>, <36>, <37>, <44>, <45>, <53>, <54> or <56>, wherein the solvent for dissolving or dispersing a hydrated crystal of a compound (I) is an aromatic hydrocarbon.

<58> The method according to any one of <10> to <55>, wherein n is 1.

<59> The method according to <58>, wherein $R^1$ is situated at the 4-position of a benzene ring.

<60> The method according to any one of <1> to <56>, wherein $R^1$ is a halogen atom.

<61> The method according to any one of <10> to <57>, wherein n is 1, and $R^1$ is a chlorine atom situated at the 4-position of a benzene ring.

<62> The method according to any one of <10> to <37>, <40> to <45> and <48> to <61>, wherein the asymmetric catalyst is 1-(3,5-bis(trifluoromethyl)phenyl)-3-((1R,2R)-2-(dimethylamino)cyclohexyl)thiourea, 1-(3,5-bis(trifluoromethyl)phenyl)-3-((1S,2S)-2-(dimethylamino)cyclohexyl)thiourea, nickel(II)bis[(S,S)—N,N'-dibenzylcyclohexane-1,2-diamine]bromide or nickel(II)bis[(R,R)—N,N'-dibenzylcyclohexane-1,2-diamine]bromide.

<63> The method according to <62>, wherein the asymmetric catalyst is nickel(II)bis[(S,S)—N,N'-dibenzylcyclohexane-1,2-diamine]bromide or nickel(II)bis[(R,R)—N,N'-dibenzylcyclohexane-1,2-diamine]bromide.

BEST MODES FOR CARRYING OUT THE INVENTION

The present invention will be explained in detail below.

First, definitions in the formulae according to the present invention will be described.

Examples of the "halogen atom" represented by $R^1$ include a fluorine atom, chlorine atom, bromine atom and iodine atom, preferably a chlorine atom and bromine atom, and particularly preferably a chlorine atom.

The "alkyl group" represented by $R^1$ may be any of linear or branched, and is an alkyl group having a carbon number of preferably 1 to 20, more preferably 1 to 6. Examples thereof include methyl, ethyl, propyl, isopropyl, butyl, pentyl, hexyl, heptyl, octyl, decyl, nonyl, undecyl and dodecyl, preferably methyl and ethyl.

The "alkoxy group" represented by $R^1$ is a group obtained substituting a hydrogen atom of a hydroxyl group by the "alkyl group" as defined above, and examples thereof include methoxy, ethoxy, propoxy, butoxy, pentyloxy and hexyloxy, and preferably methoxy.

The "haloalkyl group" represented by $R^1$ is a group obtained by substituting a hydrogen atom of the "alkyl group" as defined above by the "halogen atom" as defined above, and the number of halogen atoms to substitute is not particularly restricted, and all hydrogen atoms of the alkyl group may be substituted. Specific examples of the "haloalkyl group" include fluoromethyl, difluoromethyl, trifluoromethyl, 1-fluoroethyl, 2-fluoroethyl, 2,2-difluoroethyl, 2,2,2-trifluoroethyl, 1-fluoropropyl, 1-fluorobutyl, 1-fluoropentyl, 1-fluorohexyl, chloromethyl, dichloromethyl, trichloromethyl, 1-chloroethyl, 2-chloroethyl, 2,2-dichloroethyl, 2,2,2-trichloroethyl, 1-chloropropyl, 1-chlorobutyl, 1-chloropentyl, 1-chlorohexyl, bromomethyl, 1-bromoethyl, 2-bromoethyl, 1-bromopropyl, iodomethyl, 1-iodoethyl, 2-iodoethyl and 1-iodopropyl, preferably, fluoromethyl, difluoromethyl and trifluoromethyl.

The "cycloalkyloxy group" represented by $R^1$ is a group obtained by substituting a hydrogen atom of a hydroxyl group by a cyclic alkyl group having a carbon number of preferably 3 to 8, more preferably 3 to 6, and examples thereof include cyclopropyloxy, cyclobutyloxy, cyclopentyloxy and cyclohexyloxy, preferably, cyclopentyloxy.

The "alkylenedioxy group" to be formed by two $R^1$s together may be any of linear or branched, and is an alkylenedioxy group having a carbon number of preferably 1 to 5, more preferably 1 to 2, and examples thereof include methylenedioxy, ethylenedioxy and tetramethylenedioxy, preferably, methylenedioxy and ethylenedioxy.

As $R^1$, preferable are halogen atoms, and a chlorine atom is particularly preferable.

n represents an integer of 0 to 3, preferably 1 to 3, particularly preferably 1. In this case, the position of $R^1$ on a benzene ring is preferably 4-position.

The "alkyl group" represented by $R^2$ may be any of linear or branched, and is an alkyl group having a carbon number of preferably 1 to 8, more preferably 1 to 4, and examples thereof include methyl, ethyl, propyl, isopropyl, butyl, pentyl, hexyl, heptyl and octyl, preferably, methyl, ethyl and 2-(2-methyl)propyl.

The present invention will be illustrated in processes shown below.
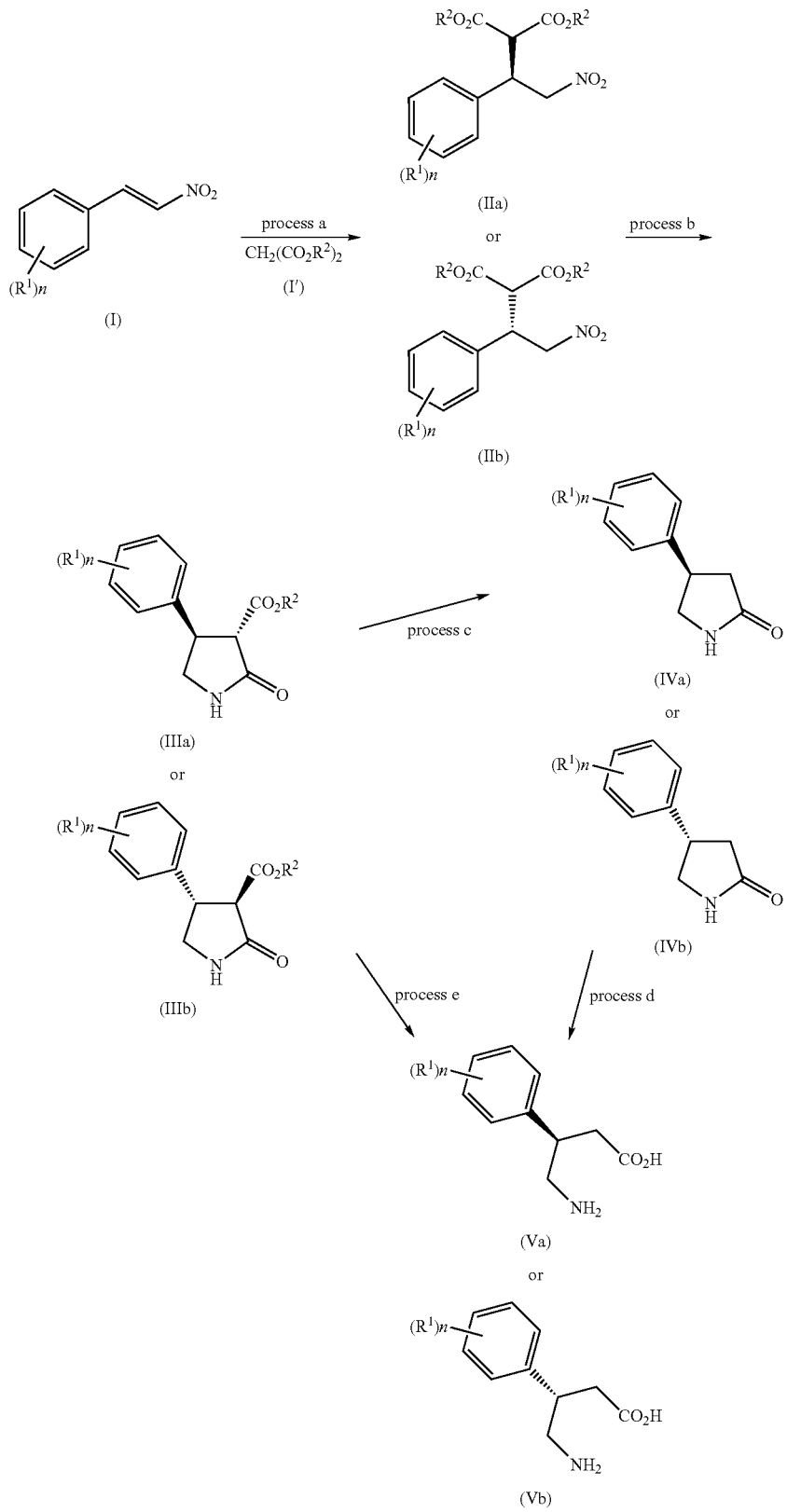
(marks in the formulae are the same as described above)

Process a

In this process, a compound (I) is reacted with a compound (I') (malonic acid diester) to produce a compound (IIa) or compound (IIb) (asymmetric Michael addition reaction).

Here, the compound (I) as a raw material may be produced by any method, and when implementation on industrial scale is taken into consideration, it is preferable to produce the compound (I) from benzaldehyde (Ia) by a method described in non-patent document 5 shown below or an analogous method since solvent extraction and the like are not necessary. The compound (I) is usually isolated as a crystal, and particularly when the compound (I) is produced by a method described in non-patent document 5, it is isolated as a hydrated crystal since the crystal is washed with water. Then, in a suitable embodiment of the present invention, before effecting the reaction of the process a, this hydrated crystal of the compound (I) is not subjected to a drying operation, and instead, the compound (I) is dissolved or dispersed in a solvent, and subjected to liquid-separation or concentration under reduced pressure or both the operations, thereby, water contained in the compound (I) is removed. By adopting such a method, there is scarce danger of explosion and the like and the compound (I) can be treated safely even in production on industrial scale since a crystal drying operation is not carried out.

The hydrated crystal of the compound (I) contains water in an amount of usually 0.05 to 3 parts by weight, preferably 0.2 to 0.8 parts by weight, further preferably 0.3 to 0.7 parts by weight with respect to 1 part by weight of the compound (I).

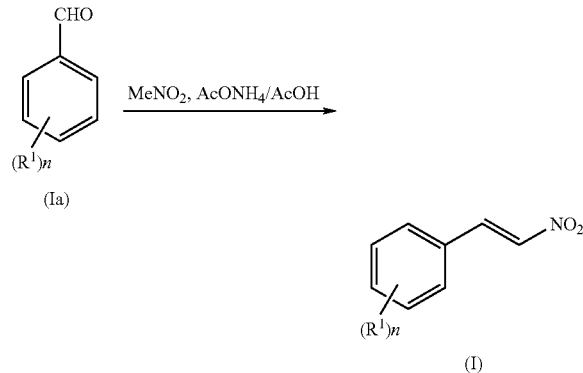

(marks in the formulae are as described above).

Examples of the above-described solvent to be used for dissolution or dispersion include aromatic hydrocarbons such as benzene, toluene and the like; ethers such as methyl t-butyl ether and the like; and esters such as ethyl acetate, methyl acetate, propyl acetate, isopropyl acetate, butyl acetate and the like, and of them, aromatic hydrocarbons are preferable, and toluene is more preferable. When operability is taken into consideration, it is preferable that this solvent is the same as a solvent to be used in an asymmetric Michael addition reaction of a malonic acid diester carried out subsequently.

The amount of the solvent is usually 1 to 50 liter, preferably 2 to 10 liter with respect to 1 kg of the compound (I) from the standpoint of extraction efficiency, solvent distillation efficiency after extraction and the like.

Water contained in the hydrated crystal of the compound (I) can be removed by at least one operation selected from (1) liquid-separation operation and (2) azeotropic operation with solvent by concentration under reduced pressure, of a solution or dispersion of the compound (I), however, it is preferable to effect both the operations (1) and (2) since water can be removed completely. In the case of adopting concentration under reduced pressure, it is necessary to appropriately select a solvent which is capable of performing azeotrope with water.

By such a method, water contained in the compound (I) is removed, then, the compound (I) is reacted with a compound (I') in the presence of an asymmetric catalyst to produce a compound (IIa) or compound (IIb). By use of an asymmetric catalyst, the compound (I') is steric-selectively added to a carbon atom at the α-position of the compound (I), thereby, either a compound (compound (IIa)) in which the steric configuration at a carbon atom at the α-position is R-configuration or a compound (compound (IIb)) in which the steric configuration at a carbon atom at the α-position is S-configuration is preferentially obtained.

This reaction is carried out usually in a solvent in the presence of an asymmetric catalyst. Though the addition order of the compound (I), compound (I') and asymmetric catalyst is not particularly restricted, it is preferable to add the compound (I') and asymmetric catalyst to the compound (I) in a solvent from the standpoint of operability.

The amount of the compound (I') is usually 0.8 to 5 mol, preferably 1.1 to 2 mol with respect to 1 mol of the compound (I) from the standpoint of yield and prevention of complication of removal of raw materials after the reaction.

The asymmetric catalyst is not particularly restricted providing it is a catalyst with which an intended compound obtained by an asymmetric Michael addition reaction (namely, compound (IIa) or compound (IIb)) is preferentially obtained. As the catalyst with which a compound (IIa) is preferentially obtained, specifically mentioned are nickel(II) bis[(S,S)—N,N'-dibenzylcyclohexane-1,2-diamine]bromide which can be prepared according to a method described in non-patent document 2 and 1-(3,5-bis(trifluoromethyl)phenyl)-3-((1R,2R)-2-(dimethylamino)cyclohexyl)thiourea described in non-patent document 1, and the like. As the catalyst with which a compound (IIb) is preferentially obtained, specifically mentioned are nickel(II)bis[(R,R)—N, N'-dibenzylcyclohexane-1,2-diamine]bromide which can be prepared according to a method described in non-patent document 2,1-(3,5-bis(trifluoromethyl)phenyl)-3-((1S,2S)-2-(dimethylamino)cyclohexyl)thiourea described in non-patent document 1, and the like. The final intended compound of the present invention is preferably a compound (Va) typified by (R)-4-amino-3-(4-chlorophenyl)butanoic acid ((R)-(−)-baclofen) useful as a reflux esophagitis remedy or antispasmodic, thus, preferable as the above-described asymmetric catalyst are catalysts with which a compound (IIa) is preferentially obtained, and particularly, nickel(II) bis[(S,S)—N,N'-dibenzylcyclohexane-1,2-diamine]bromide is preferable.

The amount of the asymmetric catalyst is usually 0.001 to 0.2 mol, preferably 0.005 to 0.1 mol with respect to 1 mol of a compound (I) from the standpoint of yield and economy.

Examples of the solvent to be used in this reaction include aromatic hydrocarbons such as benzene, toluene and the like; ethers such as tetrahydrofuran, methyl t-butyl ether, 1,2-dimethoxymethane, 1,4-dioxane, diglyme and the like; alcohols such as methanol, ethanol, isopropyl alcohol, propanol, 1-butanol, isobutanol, t-butanol and the like; and esters such as ethyl acetate, methyl acetate, propyl acetate, isopropyl acetate, butyl acetate and the like, and of them, aromatic hydrocarbons are preferable and toluene is more preferable. When the compound (I) is prepared into a solution or dispersion and liquid-separation operation and/or azeotrope operation with a solvent by concentration under reduced pressure is carried out, the solvent to be used in this process is preferably the same as the solvent used in this solution or dispersion when operability is taken into consideration. If necessary, the same or different solvents described above may be added.

The amount of the solvent is usually 0.5 to 50 liter, preferably 2 to 5 liter with respect to 1 kg of a compound (I) from the standpoint of stirring efficiency, reaction delay prevention.

The reaction temperature is usually 0 to 110° C., preferably 15 to 80° C. The reaction time is usually 30 minutes to 72 hours, preferably 1 to 24 hours, depending on the reaction temperature, reagent use amount and the like.

Isolation of a compound (IIa) or compound (IIb) can be carried out by subjecting the reaction liquid to a post treatment according to an ordinary method (for example, neutralization, extraction, washing with water, crystallization and the like). The compound (IIa) or compound (IIb) can be purified by recrystallization, extraction purification, adsorption treatment with activated carbon, silica, alumina and the like, chromatography methods such as silica gel column chromatography and the like, however, for example, the extraction solution itself, without particular purification, can be subjected to the subsequent process, or the residue after removal of a solvent can be itself subjected to the subsequent process.

As described above, however, since the compound (IIa) or compound (IIb) is also a compound having a nitro group, it is dangerous particularly on industrial scale to isolate this as a crystal and the like and dry this. Then, in a suitable embodiment of the present invention, a compound (IIa) or compound (IIb) is obtained in the form of solution or suspension without isolating as a crystal and the like, and as it is, subjected to the subsequent process b, namely, reduction and cyclization. The concentration of the compound (IIa) or compound (IIb) in the solution or suspension is maintained to preferably 80 wt % or less, further preferably 70 wt % or less. From the standpoint of reaction efficiency, production efficiency and the like in the subsequent process, it concentration is preferably 10 wt % or more, further preferably 20 wt % or more.

Here, it is preferable that the compound (IIa) or compound (IIb) is not finally made into a form of crystal and the like, and after completion of the reaction, the reaction liquid is subjected to a normal post treatment (neutralization, liquid-separation, extraction and the like).

Examples of the solvent to be used in the solution or suspension include aromatic hydrocarbons such as benzene, toluene and the like; ethers such as tetrahydrofuran, methyl t-butyl ether, 1,2-dimethoxymethane, 1,4-dioxane, diglyme and the like; alcohols such as methanol, ethanol, isopropyl alcohol, propanol, 1-butanol, isobutanol, t-butanol and the like; esters such as ethyl acetate, methyl acetate, propyl acetate, isopropyl acetate, butyl acetate and the like; and water, and of them, aromatic hydrocarbons and alcohols are preferable and toluene and methanol are more preferable. When operability is taken into consideration, this solvent is preferably the same as a solvent to be used in the subsequent process b.

The amount of the solvent to be used in the solution or suspension is usually 1 to 50 liter, preferably 2 to 10 liter with respect to 1 kg of a compound (IIa) or compound (IIb) from the standpoint of extraction efficiency, solvent distillation efficiency and the like.

The compound (IIa) or compound (IIb) contains, in addition to a compound having intended steric configuration, a compound having steric configuration opposite to the above-described compound in some cases (namely, when the intended compound is a compound (IIa), a compound (IIb) is contained in some cases, and when the intended compound is a compound (IIb), a compound (IIa) is contained in some cases), and in such a case, purification is necessary, and though purification may be carried out when the compound (IIa) or compound (IIb) is obtained, it is preferable to carry out purification after deriving into a compound (IIIa) or compound (IIIb) in the subsequent process c from the standpoint of easiness of purification, and the like.

Process b

In this process, a compound (IIa) or compound (IIb) is reduced and cyclized to produce a compound (IIIa) or compound (IIIb). Here, when a compound (IIa) or compound (IIb) is reduced, cyclization thereof also progresses consecutively, leading to production of a compound (IIIa) or compound (IIIb).

The reduction of a compound (IIa) or compound (IIb) can be carried out usually in a solvent using a reducing agent, alternatively, by catalytic hydrogen reduction in a solvent in the presence of a metal catalyst.

Addition of a compound (IIa) or compound (IIb) into the reaction system is usually carried out in the form of solution or suspension wherein the concentration thereof is maintained in the range of 10 to 80 wt %, preferably 20 to 70 wt % from the process a consecutively, and also in the reaction of this process, the concentration of a compound (IIa) or compound (IIb) in the reaction system is maintained in the range of usually 10 to 80 wt %, preferably 20 to 70 wt %.

In the case of reduction with a reducing agent, a compound (IIa) or compound (IIb) is mixed with a reducing agent in a solvent.

Examples of the reducing agent include metal hydrides such as sodium borohydride, potassium borohydride, lithium borohydride, lithium aluminum hydride, diisobutylaluminum hydride, sodium bis(2-methoxyethoxy)aluminum hydride and the like; combinations of the metal hydrides with Lewis acids such as boron trifluoride and the like, Broensted acids such as sulfuric acid and the like; borane-THF complex; and borane-dimethyl sulfide complex, and of them, a combination of sodium borohydride with a di-valent nickel salt, and sodium bis(2-methoxyethoxy)aluminum hydride are preferable and a combination of sodium borohydride with a di-valent nickel salt is particularly preferable.

The amount of the reducing agent is usually 0.5 mol to 20 mol, preferably 1 mol to 12 mol with respect to 1 mol of a compound (IIa) or compound (IIb) from the standpoint of prevention of production of a large amount of by-product, prevention of lowering of yield and the like.

Examples of the solvent include alcohols such as methanol, ethanol and the like; and ethers such as tetrahydrofuran, methyl t-butyl ether, 1,2-dimethoxymethane, 1,4-dioxane, diglyme and the like, and of them, methanol and tetrahydrofuran are preferable. When a compound (IIa) or compound (IIb) is obtained in the form of solution or suspension, the solvent to be used in this reduction is preferably the same as the solvent used in the solution or suspension when operability is taken into consideration. If necessary, the same or different solvents described above may be added.

The amount of the solvent is usually 0.5 to 50 liter, preferably 2 to 5 liter with respect to 1 kg of a compound (IIa) or compound (IIb) from the standpoint of stirring efficiency, reaction delay prevention.

The reaction temperature is usually −78 to 50° C., preferably −10 to 30° C. The reaction time is usually 30 minutes to 24 hours, preferably 1 to 10 hours depending on the reaction temperature, reagent use amount and the like.

In the case of catalytic hydrogen reduction, hydrogen is introduced into a mixed solution containing a compound (IIa) or compound (IIb) and a metal catalyst in a solvent.

Examples of the metal catalyst include palladium-carbon, rhodium-carbon, platinum-carbon, development cobalt and developed nickel, and of them, development cobalt and developed nickel are preferable and developed nickel is more preferable. In a compound in which $R^1$ is a halogen atom, a halogen atom is released by reduction in some cases. When this compound is reduced without this releasing of a halogen atom, use of developed nickel containing iron is preferable. In developed nickel containing iron, it is preferable that the iron content is 0.1 to 50 wt %, particularly 10 to 30 wt %.

The amount of the metal catalyst is usually 0.01 to 5 kg, preferably 0.1 to 1 kg with respect to 1 kg of a compound (IIa) or compound (IIb) from the standpoint of prevention of lowering of yield due to delay or incompletion of the reaction, prevention of increase of by-product and the like.

Examples of the solvent to be used in catalytic hydrogen reduction include ethers such as tetrahydrofuran, methyl t-butyl ether, 1,2-dimethoxymethane, 1,4-dioxane, diglyme and the like; alcohols such as methanol, ethanol, isopropyl alcohol, propanol, 1-butanol, isobutanol, t-butanol and the like; esters such as ethyl acetate, methyl acetate, propyl acetate, isopropyl acetate, butyl acetate and the like; organic acids such as acetic acid, propionic acid and the like; water; and mixed solvents thereof, and of them, alcohols are preferable and methanol and ethanol are particularly preferable. When a compound (IIa) or compound (IIb) is obtained in the form of solution or suspension, the solvent to be used in this reduction is preferably the same as the solvent used in the solution or suspension when operability is take into consideration. If necessary, the same or different solvents described above may be added.

The amount of the solvent to be used in catalytic hydrogen reduction is usually 0.5 to 50 liter, preferably 2 to 10 liter with respect to 1 kg of a compound (IIa) or compound (IIb) from the standpoint of stirring efficiency, reaction delay prevention and the like.

The reaction temperature in catalytic hydrogen reduction is usually 0 to 110° C., preferably 15 to 60° C. The reaction time in catalytic hydrogen reduction is usually 30 minutes to 48 hours, preferably 1 to 24 hours depending on the reaction temperature, reagent use amount and the like.

The reduction reaction in this process is preferably a catalytic hydrogen reduction reaction, and particularly, in the case of a compound in which $R^1$ is a halogen atom, a catalytic hydrogen reduction reaction using developed nickel containing iron is preferable.

Isolation of a compound (IIIa) or compound (IIIb) can be carried out by subjecting the reaction liquid to a post treatment according to an ordinary method (for example, neutralization, extraction, washing with water, distillation, crystallization and the like). The compound (IIIa) or compound (IIIb) can be purified by recrystallization, extraction purification, distillation, adsorption treatment with activated carbon, silica, alumina and the like, chromatography methods such as silica gel column chromatography and the like, however, for example, the extraction solution itself, without particular purification, can be subjected to the subsequent process, or the residue after removal of a solvent can be itself subjected to the subsequent process.

In the case of purification by recrystallization, a steric isomer of a compound (IIIa) or compound (IIIb) is crystallized while isomerizing during crystallization in a crystallizing solvent by adding a base to the recrystallization solvent, resultantly, the yield of a compound (IIIa) or compound (IIIb) can also be increased.

Examples of the recrystallization solvent include alcohol solvents such as methanol, ethanol, 2-propanol, 1-butanol, 2-butanol, isobutyl alcohol, t-butanol and the like; ester solvents such as ethyl acetate, isopropyl acetate, n-butyl acetate, isobutyl acetate, t-butyl acetate and the like; ketone solvents such as acetone, methyl ethyl ketone, methyl isobutyl ketone and the like; aromatic hydrocarbon solvents such as toluene, xylene and the like; halogenated substituted aromatic hydrocarbon solvents such as chlorobenzene, fluorobenzene and the like; aliphatic hydrocarbon solvents such as hexane, heptane, cyclohexane and the like; and mixed solvents thereof. Of them, alcohol solvents such as methanol, ethanol, 2-propanol and the like are preferable and 2-propanol is particularly preferable.

Examples of the base to be added include organic amines such as triethylamine, N,N-diisopropylethylamine, pyridine and the like; metal alkoxides such as sodium methylate, potassium methylate, sodium ethylate and the like; and inorganic bases such as sodium hydrogen carbonate, sodium carbonate, sodium hydroxide, potassium hydroxide, cesium carbonate, cesium hydroxide and the like. Of them, triethylamine and sodium methylate are preferable. The amount of the base is 0.01 mol % to 100 mol %, preferably 0.1 mol % to 10 mol % with respect to a compound (IIIa) or compound (IIIb).

Process c

In this process, a compound (IIIa) or compound (IIIb) is hydrolyzed and decarboxylated, to produced a compound (IVa) or compound (IVb). The hydrolysis of a compound (IIIa) or compound (IIIb) is carried out usually by treating with a base in a solvent.

Examples of the base include sodium hydroxide, potassium hydroxide, lithium hydroxide, potassium carbonate and sodium carbonate, and of them, sodium hydroxide and potassium hydroxide are preferable.

The amount of the base is usually 0.5 to 5 mol, preferably 1 to 1.5 mol with respect to 1 mol of a compound (IIIa) or compound (IIIb) from the standpoint of prevention of lowering of yield due to incompletion of the reaction, prevention of increase of by-product and the like.

Examples of the solvent include alcohols such as methanol, ethanol and the like; ethers such as tetrahydrofuran, 1,2-dimethoxymethane, 1,4-dioxane, diglyme and the like; and water, and of them, alcohols are preferable and methanol is more preferable.

The amount of the solvent is usually 0.5 to 50 liter, preferably 2 to 10 liter with respect to 1 kg of a compound (IIIa) or compound (IIIb) from the standpoint of stirring efficiency, reaction delay prevention.

The reaction temperature is usually −30 to 50° C., preferably 0 to 30° C. The reaction time is usually 10 minutes to 24 hours, preferably 1 to 10 hours depending on the reaction temperature, reagent use amount and the like.

After completion of the reaction, the reaction liquid can be isolated by subjecting to a post treatment according to an ordinary method (for example, neutralization, extraction and the like). It can be purified by recrystallization, extraction purification, distillation, adsorption treatment with activated carbon, silica, alumina and the like, chromatography methods such as silica gel column chromatography and the like, however, for example, the extraction solution itself, without particular purification, can be subjected to the subsequent process, or the residue after removal of a solvent can be itself subjected to the subsequent process.

By hydrolyzing a compound (IIIa) or compound (IIIb), then, decarboxylating this, a compound (IVa) or compound (IVb) can be produced. Here, decarboxylation is carried out by heating a hydrolysate of a compound (IIIa) or compound (IIIb), and specifically, it can be carried out by adding (preferably, dropping) a solution of a hydrolysate of a compound (IIIa) or compound (IIIb) to a solvent and heating the mixture.

The solvent to be used in decarboxylation is not particularly restricted providing it is a solvent suitable for heating, and examples thereof include aromatic hydrocarbons such as toluene, xylene, mesitylene and the like, and aromatic halides such as dichlorobenzene, dibromobenzene and the like, and of them, aromatic hydrocarbons are preferable and xylene is particularly preferable.

The amount of the solvent to be used in decarboxylation is usually 0.5 to 50 liter, preferably 2 to 10 liter with respect to 1 kg of a compound (IIIa) or compound (IIIb) from the standpoint of stirring efficiency, reaction delay prevention.

The reaction temperature in decarboxylation is usually 25 to 200° C., preferably 90 to 150° C. It is preferable to heat the solvent previously to the reaction temperature before addition of a solution of a hydrolysate of a compound (IIIa) or compound (IIIb). The reaction time in decarboxylation is usually 30 minutes to 24 hours, preferably 1 to 10 hours depending on the reaction temperature, reagent use amount and the like.

If necessary, the above-described addition may be carried out while distilling the solvent in a solution of a hydrolysate of a compound (IIIa) or compound (IIIb) off from the reaction system.

Isolation of a compound (IVa) or compound (IVb) can be carried out by subjecting the reaction liquid to a post treatment according to an ordinary method (for example, neutralization, extraction, washing with water, distillation, crystallization and the like). The compound (IVa) or compound (IVb) can be purified by recrystallization, extraction purification, distillation, adsorption treatment with activated carbon, silica, alumina and the like, chromatography methods such as silica gel column chromatography and the like, however, for example, the extraction solution itself, without particular purification, can be subjected to the subsequent process, or the residue after removal of a solvent can be itself subjected to the subsequent process.

Process d

In this process, a compound (IVa) or compound (IVb) is ring-opened to produce a compound (Va) or compound (Vb). Specifically, a compound (IVa) or compound (IVb) is treated with an acid. This process is usually carried out without solvent.

Examples of the acid include inorganic acids such as hydrochloric acid, sulfuric acid, nitric acid and the like, and organic sulfonic acids such as methanesulfonic acid, toluenesulfonic acid and the like, and of them, hydrochloric acid is preferable.

The amount of the acid is usually 0.5 to 50 mol, preferably 2 to 20 mol with respect to 1 mol of a compound (IVa) or compound (IVb) from the standpoint of yield, post treatment efficiency and the like.

The reaction temperature is usually 25 to 180° C., preferably 60 to 120° C. The reaction time is usually 30 minutes to 48 hours, preferably 1 to 24 hours depending on the reaction temperature, reagent use amount and the like.

Isolation of a compound (Va) or compound (Vb) can be carried out by subjecting the reaction liquid to a post treatment according to an ordinary method (for example, neutralization, extraction, washing with water, crystallization and the like). The compound (Va) or compound (Vb) can be purified by recrystallization, extraction purification, adsorption treatment with activated carbon, silica, alumina and the like, chromatography methods such as silica gel column chromatography and the like.

Process e

A compound (Va) or compound (Vb) can also be produced directly by treating a compound (IIIa) or compound (IIIb) with an acid.

When a compound (IIIa) or compound (IIIb) is treated with an acid, carbon dioxide is generated as described above. In a suitable embodiment of the present invention, a compound (IIIa) or compound (IIIb) is once dissolved or dispersed in a solvent, and this solution or dispersion is added (preferably, dropped) to an acid, thereby, generation of carbon dioxide is controlled.

Examples of the solvent for dissolving or dispersing a compound (IIIa) or compound (IIIb) include aromatic halides such as 1,2-dichlorobenzene, 1,3-dichlorobenzene and the like; and aromatic halides such as toluene, xylene, mesitylene and the like, and of them, aromatic halides are preferable and 1,2-dichlorobenzene is particularly preferable.

The amount of the solvent is usually 0.5 to 50 liter, preferably 2 to 10 liter with respect to 1 kg of a compound (IIIa) or compound (IIIb) from the standpoint of stability of the solution or dispersion, reaction delay prevention and the like.

Examples of the acid include inorganic acids such as hydrochloric acid, sulfuric acid, nitric acid and the like, and organic sulfonic acids such as methanesulfonic acid, toluenesulfonic acid and the like, and of them, hydrochloric acid is preferable.

The amount of the acid is usually 0.5 to 50 mol, preferably 2 to 20 mol with respect to 1 mol of a compound (IIIa) or compound (IIIb) from the standpoint of yield, post treatments efficiency and the like.

The reaction temperature is usually 25 to 180° C., preferably 60 to 120° C. The acid may be regulated at the reaction temperature previously before addition of a solution or dispersion of a compound (IIIa) or compound (IIIb), alternatively, a mixture may be heated after addition of a solution or dispersion of a compound (IIIa) or compound (IIIb). The reaction time is usually 30 minutes to 48 hours, preferably 1 to 24 hours depending on the reaction temperature, reagent use amount and the like.

In a series of process in the present invention, the steric configuration at the α-position of a compound (IIa) or compound (IIb) is retained without change until a compound (Va) or compound (Vb).

The compound (Va) or compound (Vb) may take a form of salt. Examples of the salt include salts of bases such as alkali metal salts (for example, sodium salt, potassium salt and the like), alkaline earth metal salts (for example, calcium salt, magnesium salt and the like), organic base salts (for example, trimethylamine salt, triethylamine salt, pyridine salt, picoline salt, dicyclohexylamine salt and the like) and the like, and acid addition salts such as inorganic acid addition salts (for example, hydrochloric acid addition salt, hydrobromic acid addition salt, nitric acid addition salt, sulfuric acid addition salt, phosphoric acid addition salt and the like), organic acid addition salts (for example, formic acid addition salt, acetic acid addition salt, oxalic acid addition salt, malonic acid addition salt, citric acid addition salt, fumaric acid addition salt, lactic acid addition salt, malic acid addition salt, succinic acid addition salt, tartaric acid addition salt, trifluoroacetic acid addition salt and the like) and the like.

Thus obtained compound (Va) or compound (Vb), particularly, (R)-4-amino-3-(4-chlorophenyl)butanoic acid ((R)-(−)-baclofen) is a compound useful as a reflux esophagitis remedy or antispasmodic.

The present invention will be explained further in detail by examples mentioned below, but the present invention is not limited to these example.

EXAMPLE 1

Synthesis of dimethyl (R)-2-(1-(4-chlorophenyl)-2-nitroethyl)malonate

Under a nitrogen atmosphere, 4-chlorobenzaldehyde (2.5 g, 18 mmol) and ammonium acetate (2.5 g, 32 mmol) were dissolved in acetic acid (19 ml), and the solution was heated up to 90° C. Nitromethane (5.4 g, 89 mmol) was dropped at 90° C. over a period of 1 hour, and the mixture was stirred at the same temperature for 4 hours. The mixture was cooled to 50° C., and at the same temperature, water (19 ml) was dropped over a period of 1 hour, to deposit a coarse crystal of 4-chloro-β-nitrostyrene. After completion of dropping, the mixture was stirred at room temperature for 1 hour, further cooled to 10° C., and stirred at the same temperature for 1 hour, then, a crystal was filtrated and washed with water (19 ml) to obtain 4.32 g of a hydrated coarse crystal of 4-chloro-β-nitrostyrene (water amount: 1.7 g (water content: 40%), 4-chloro-β-nitrostyrene content: 2.61 g).

This hydrated coarse crystal of 4-chloro-β-nitrostyrene was dissolved in toluene (19 ml), the aqueous phase was separated by a liquid-separation operation, and the organic phase was azeotropically dehydrated under reduced pressure, to distill off 9.5 ml. A catalyst prepared according to a method described in non-patent document 2 (nickel(II)bis[(S,S)—N, N'-dibenzylcyclohexane-1,2-diamine]bromide) (58 mg, 0.072 mmol) and dimethyl malonate (2.3 g, 17 mmol) were added, and the mixture was heated up to 50° C. and stirred at the same temperature for 7 hours. After completion of the reaction, the reaction solution was washed with 0.1 mol/L hydrochloric acid (5 ml) and water (5 ml) each once. The organic phase was concentrated under reduced pressure, and crystallized in a toluene/heptane solvent, to obtain 4.2 g (13 mmol) of a title compound. Yield 75%. The spectrum data corresponded to the value in non-patent document 3. The optical purity of the resultant title compound was measured by HPLC to find a value of 94% ee.
HPLC Analysis Condition;
column: CHIRALCEL OD-H 4.6×250 mm
mobile phase A: hexane, B: 2-propanol, A/B=80/20
flow rate: 0.6 ml/min
detector: UV 220 nm

EXAMPLE 2

Synthesis of methyl (3S,4R)-4-(4-chlorophenyl)-2-oxopyrrolidine-3-carboxylate

To 210 ml of methanol was added 42.0 g (133 mmol) of dimethyl (R)-2-(1-(4-chlorophenyl)-2-nitroethyl)malonate and developed nickel (21 g), and the mixture was reacted at 35° C. for 8 hours under a hydrogen pressure of 0.5 Mpa (gauge pressure). After completion of the reaction, the nickel catalyst was filtrated, and the filtrate was concentrated under reduced pressure. Ethyl acetate and water were added to cause liquid-separation, the organic layer was concentrate under reduced pressure, and crystallized from heptanes/ethyl acetate. The resultant crystal was filtrated, and dried under reduced pressure, to obtain 28.8 g (114 mmol) of a title compound.
Yield: 85%. mp 166° C.
$^1$H NMR (CDCl$_3$, 400 MHz) δ 7.34-7.31 (2H, m), 7.22-7.18 (2H, m), 4.09 (1H, dd, J=8.0 Hz, 8.4 Hz), 3.84-3.81 (1H, m), 3.79 (3H, s), 3.54 (1H, d, J=10.0 Hz), 3.40 (1H, dd, J=8.0 Hz, 8.4 Hz) $^{13}$C NMR (CDCl$_3$, 100 MHz) δ 172.3, 169.2, 138.0, 133.4, 129.1, 128.3, 55.1, 52.9, 47.6, 43.7

The optical purity of the resultant title compound was measured by HPLC to find a value of 99% ee.
HPLC Analysis Condition;
column: CHIRALPAK AD-H 4.6×250 mm
mobile phase A: hexane, B: 2-propanol, A/B=80/20
flow rate: 0.6 ml/min
detector: UV 220 nm

EXAMPLE 3

Synthesis of (R)-4-(4-chlorophenyl)pyrrolidin-2-one

Under a nitrogen atmosphere, to methanol (220 ml) was added methyl (3S,4R)-4-(4-chlorophenyl)-2-oxopyrrolidine-3-carboxylate (28.0 g, 110 mmol), and 2 mol/L sodium hydroxide aqueous solution (66 ml) was dropped over a period of 1 hour. After completion of dropping, the mixture was further stirred for 1 hour, and neutralized with 2 mol/L hydrochloric acid (71 ml), and methanol was distilled off under reduced pressure. The residue was extracted with ethyl acetate (150 ml×2), to obtain an ethyl acetate solution containing (3S,4R)-4-(4-chlorophenyl)-2-oxopyrrolidine-3-carboxylic acid. This solution was dropped over a period of 4 hours into xylene (150 ml) heated at 130 to 140° C. while distilling off ethyl acetate. After completion of the reaction, xylene (100 ml) was added, and the mixture was filtrated and concentrated under reduced pressure. Crystallization from xylene/heptanes was performed to obtain 19.3 g (98.6 mmol) of a title compound. Yield: 90%. The spectrum data corresponded to the value in non-patent document 1. The optical purity of the resultant title compound was measured by HPLC to find a value of 99% ee.
HPLC Analysis Condition;
column: CHIRALPAK AD-H 4.6×250 mm
mobile phase A: hexane, B: 2-propanol, A/B=80/20
flow rate: 0.6 ml/min
detector: UV 220 nm

EXAMPLE 4

Synthesis of (R)-4-amino-3-(4-chlorophenyl)butanoic acid hydrochloride

Under a nitrogen atmosphere, to (R)-4-(4-chlorophenyl)pyrrolidin-2-one (5.0 g, 26 mmol) was added 6 mol/L hydrochloric acid (18 g), and the mixture was heated up to 100° C. The mixture was stirred at the same temperature for 10 hours, then, concentrated under reduced pressure, to deposit a crystal of a title compound. 2-propanol (15 ml) was added, and the mixture was concentrated again, then, 2-propanol (30 ml) was added, and the mixture was stirred at room temperature for 1 hour. The crystal was filtrated and washed with 2-propanol (5 ml) to obtain 4.9 g (20 mmol) of a title compound. Yield: 77%. The spectrum data corresponded to the value in non-patent document 1. The optical purity of the resultant title compound was measured by HPLC to find a value of 99.9% ee.
HPLC Analysis Condition;
column: CROWNPAK CR(+) 4.6×250 mm
mobile phase: water having a pH adjusted to 2 with HClO$_4$
flow rate: 2.0 ml/min
detector: UV 220 nm

EXAMPLE 5

Synthesis of methyl (3S,4R)-4-(4-chlorophenyl)-2-oxopyrrolidine-3-carboxylate

Under a nitrogen atmosphere, 4-chlorobenzaldehyde (20 g, 142 mmol) and ammonium acetate (19.8 g, 257 mmol) were dissolved in acetic acid (150 ml), and the solution was heated up to 90° C. Nitromethane (43.4 g, 711 mmol) was dropped at 90° C. over a period of 1 hour, and the mixture was stirred for 4 hours. The mixture was cooled to 50° C., and water (150 ml) was dropped over a period of 1 hour, to deposit a coarse crystal of 4-chloro-β-nitrostyrene. After completion of dropping, the mixture was stirred at room temperature for 1 hour, further cooled to 10° C., stirred at the same temperature for 1 hour, then, a crystal was filtrated and washed with water (150 ml) to obtain 40.1 g of a hydrated coarse crystal of 4-chloro-β-nitrostyrene (4-chloro-β-nitrostyrene content: 20.9 g, water content: 47.9%).

This hydrated coarse crystal of 4-chloro-β-nitrostyrene was dissolved in toluene (150 ml), the aqueous phase was separated by a liquid-separation operation, and the organic phase was azeotropically dehydrated under reduced pressure, to distill off about 80 ml.

A catalyst prepared according to a method described in non-patent document 2 (nickel(II)bis[(S,S)—N,N'-dibenzyl-cyclohexane-1,2-diamine]bromide) (460 mg, 0.57 mmol) and dimethyl malonate (18.1 g, 137 mmol) were added, and the mixture was heated up to 50° C. and stirred at the same temperature for 7 hours. After completion of the reaction, the reaction solution was washed with 0.1 mol/L hydrochloric acid (30 ml) and water (30 ml) each once. The resultant organic phase had a weight of 121.9 g.

26.0 g of this was partially taken out, and a part of the solvent was distilled off under reduced pressure (content of compound (IIa): 55 wt %), then, 25 ml of methanol and developed nickel (2.4 g) were added. Under a hydrogen pressure of 0.5 MPa (gauge pressure), the mixture was reacted at 35° C. for 6 hours. After completion of the reaction, the nickel catalyst was filtrated, and the filtrate was concentrated under reduced pressure. Ethyl acetate and water were added to cause liquid-separation, the organic layer was concentrated under reduced pressure, and crystallized from heptane/ethyl acetate. The resultant crystal was filtrated, and dried under reduced pressure, to obtain 4.60 g (18.1 mmol) of a title compound. A yield of 60% (yield from 4-chlorobenzaldehyde) and physical properties corresponded to values in Example 2. The optical purity of the resultant title compound was measured by HPLC to find a value of 99% ee.
HPLC Analysis Condition;
column: CHIRALPAK AD-H 4.6×250 mm
mobile phase A: hexane, B: 2-propanol, A/B=80/20
flow rate: 0.6 ml/min
detector: UV 220 nm

EXAMPLE 6

Synthesis of (R)-4-amino-3-(4-chlorophenyl)butanoic acid hydrochloride

Under a nitrogen atmosphere, methyl (3S,4R)-4-(4-chlorophenyl)-2-oxopyrrolidine-3-carboxylate (5.00 g, 19.7 mmol) was suspended in 1,2-dichlorobenzene (25 ml), and the suspension was dropped over a period of about 3 hours into 6 mol/L hydrochloric acid (20 g) heated up to 100° C. The mixture was reacted for 10 hours, then, cooled to 80° C., and the organic layer was separated by a liquid-separation operation. The aqueous layer was concentrated under reduced pressure, acetonitrile (15 ml) was added, and the mixture was concentrated again, then, acetonitrile (30 ml) was added, and the mixture was stirred at room temperature for 1 hour. The crystal was filtrated and washed with acetonitrile (5 ml) to obtain 4.00 g (16.0 mmol) of a title compound (yield: 81%).

The spectrum data corresponded to the value in Example 4. The optical purity of the resultant title compound was measured by HPLC to find a value of 99.9% ee.
HPLC Analysis Condition;
column: CROWNPAK CR(+) 4.6×250 mm
mobile phase: water having a pH adjusted to 2 with $HClO_4$
flow rate: 2.0 ml/min
detector: UV 220 nm

EXAMPLE 7

Synthesis of methyl (3S,4R)-4-(4-chlorophenyl)-2-oxopyrrolidine-3-carboxylate

Using dimethyl (R)-2-(1-(4-chlorophenyl)-2-nitroethyl)malonate (70.0 g, 222 mmol), a reaction was carried out in the same manner as in Example 2, to obtain a title compound (yield: 80%). The spectrum data corresponded to the value in Example 2. The optical purity of the resultant compound was measured by HPLC to find a value of 94.86% ee. The content of a by-product obtained by releasing a chlorine atom was 0.94% (conditions are shown below).
HPLC Analysis Condition;
column: CAPCELL PAK C8 DD 4.6×150 mm
mobile phase A: 0.1% phosphoric acid aqueous solution, B: acetonitrile
gradient: B (10%, 0 minute)→B (60%, 20 minutes)
flow rate: 1.0 ml/min
detector: UV 210 nm The optical purity of the resultant title compound was measured by HPLC to find a value of 99.9% ee or more (conditions are shown below).
HPLC Analysis Condition;
column: CHIRALCEL AD-H 4.6×250 mm
mobile phase A: hexane, B: 2-propanol, A/B=80/20
flow rate: 0.6 ml/min
detector: UV 220 nm

EXAMPLE 8

Synthesis of methyl (3S,4R)-4-(4-chlorophenyl)-2-oxopyrrolidine-3-carboxylate

To 2-propanol (250 ml) was added dimethyl (R)-2-(1-(4-chlorophenyl)-2-nitroethyl)malonate (50.0 g, 158 mmol) and iron-containing developed nickel (5.0 g, containing iron 16.6%, aluminum 6.1%, manufactured by Kawaken Fine Chemical K.K.), and the mixture was reacted at 65° C. for 3 hours under a hydrogen pressure of 0.5 MPa (gauge pressure). After completion of the reaction, tetrahydrofuran (175 ml) was added, and the nickel catalyst was filtrated off. The nickel catalyst was washed with tetrahydrofuran (75 ml), and filtrate and washing liquid were combined, and acidic active alumina (5.0 g) was added to this and the mixture was thermally insulated at 50 to 60° C. The active alumina was filtrated off, then, the filtrate was concentrate under reduced pressure. The concentrated filtrate was cooled to 8° C., then, the resultant crystal was filtrated, and dried under reduced pressure, to obtain a title compound (31.4 g, 124 mmol) (yield: 78%). The spectrum data corresponded to the value in Example 2. The optical purity of the resultant compound was measured by HPLC to find a value of 99.73% ee. The content of a by-product obtained by releasing a chlorine atom was 0.06% (conditions are shown below).
HPLC Analysis Condition;
column: CAPCELL PAK C8 DD 4.6×150 mm mobile phase A: 0.1% phosphoric acid aqueous solution, B: acetonitrile
gradient: B (10%, 0 minute)→B (60%, 20 minutes)
flow rate: 1.0 ml/min
detector: UV 210 nm The optical purity of the resultant title compound was measured by HPLC to find a value of 99.9% ee or more (conditions are shown below).
HPLC Analysis Condition;
column: CHIRALCEL AD-H 4.6×250 mm
mobile phase A: hexane, B: 2-propanol, A/B=80/20
flow rate: 0.6 ml/min
detector: UV 220 nm

EXAMPLE 9

Synthesis of
(R)-4-amino-3-(4-chlorophenyl)butanoic acid

Under a nitrogen atmosphere, methyl (3S,4R)-4-(4-chlorophenyl)-2-oxopyrrolidine-3-carboxylate (3.80 g, 15.0 mmol) was suspended in 1,2-dichlorobenzene (25 ml), and the suspension was poured into 6 mol/L hydrochloric acid (15.2 g). The mixture was reacted at 105° C. for 9 hours, then, cooled to 80° C. and the organic layer was separated by a liquid-separation operation. The aqueous layer was washed with 1,2-dichlorobenzene (11 ml), then, neutralized with a 20% sodium hydroxide aqueous solution to adjust pH to 7. The mixture was cooled to 15° C. and thermally insulated for 1 hour, then, the crystallized crystal was filtrated, and dried under reduces pressure, to obtain a title compound (2.69 g, 12.6 mmol)(yield: 84%). The optical purity of the resultant title compound was measured by HPLC to find a value of 99.9% ee or more (conditions are shown below).
HPLC Analysis Condition;
column: CROWNPAK CR(+) 4.6×250 mm
mobile phase: water having a pH adjusted to 2 with $HClO_4$
flow rate: 2.0 ml/min
detector: UV 220 nm

EXAMPLE 10

Synthesis of
(R)-4-amino-3-(4-chlorophenyl)butanoic acid

Under a nitrogen atmosphere, (R)-4-amino-3-(4-chlorophenyl)butanoic acid hydrochloride (4.0 g, 16.0 mmol) was dissolved in water (12 ml). Into this, 1 mol/L sodium hydroxide aqueous solution was dropped, to adjust pH to 6.5. The crystallized crystal was filtrated and dried under reduced pressure to obtain a title compound (3.13 g, 14.6 mmol) (yield: 91%). The optical purity of the resultant title compound was measured by HPLC to find a value of 99.9% ee or more (conditions are shown below).
HPLC Analysis Condition;
column: CROWNPAK CR(+) 4.6×250 mm
mobile phase: water having a pH adjusted to 2 with $HClO_4$
flow rate: 2.0 ml/min
detector: UV 220 nm According to the production method of the present invention, nitroolefins and 2-(1-substituted phenyl-2-nitroethyl) malonic acid diesters are not required to be subjected to a drying operation, thus, these compounds can be handled safely even on industrial scale. Further, since carbon dioxide generated in a reaction of 4-substituted phenyl-2-oxopyrrolidine-3-carboxylic acid esters with a mineral acid can be controlled easily, 4-amino-3-substituted phenylbutanoic acids can be produced safely even on industrial scale.

The invention claimed is:
1. A method comprising dissolving or dispersing a compound of the formula (IIIa):

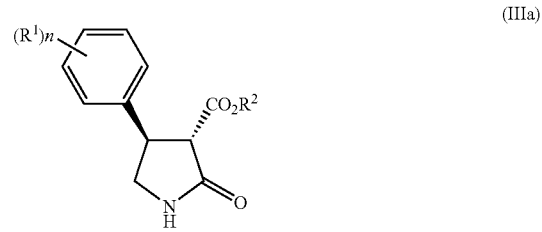

(IIIa)

(wherein, n represents an integer of 0 to 3, $R^1$ represents a halogen atom, alkyl group, alkoxy group, haloalkyl group and cycloalkyloxy group, when n is 2 or 3, $R^1$s may be the same or different, or when n is 2 or 3, two $R^1$s together form an alkylenedioxy group, $R^2$ represents an alkyl group) or a compound of the formula (IIIb):

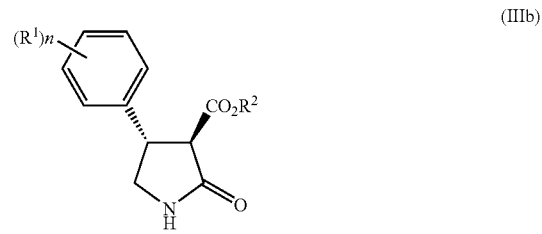

(IIIb)

(wherein, $R^1$, $R^2$ and n have the same meanings as described above)
in a solvent, and adding the resultant solution or dispersion to an acid, to produce a compound of the formula (Va):

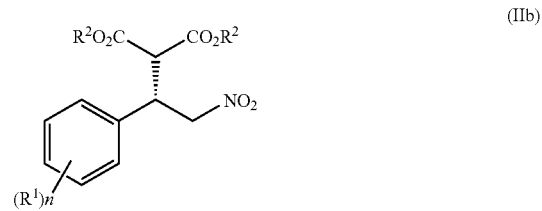

(IIb)

(wherein, $R^1$, $R^2$ and n have the same meanings as described above); and
wherein the reduction of a compound of the formula (IIa) or a compound of the formula (IIb) is catalytic hydrogen reduction in the presence of a developed nickel containing iron.

2. The method according to claim 1, wherein the solvent for dissolving or dispersing a compound of the formula (IIIa) or a compound of the formula (IIIb) is a halogenated aromatic hydrocarbon.

3. The method according to claim 1, wherein the iron content of the developed nickel containing iron is 0.1 to 50 wt %.

4. The method according to claim 1, wherein the compound of the formula (IIa) or the compound of the formula (IIb) is obtained by reacting a compound of the formula (I):

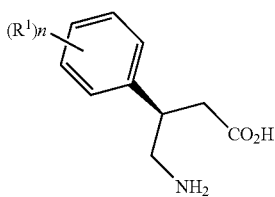

(Va)

(wherein, $R^1$ and n have the same meanings as described above) or a compound of the formula (Vb):

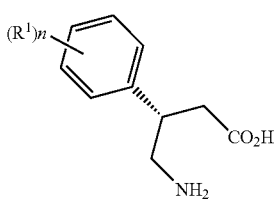

(Vb)

(wherein, $R^1$ and n have the same meanings as described above);

wherein the compound of the formula (IIIa) or the compound of the formula (IIIb) is obtained by reducing and cyclizing a compound of the formula (IIa):

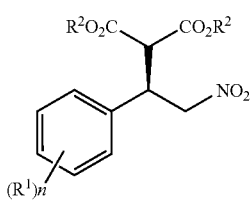

(IIa)

(wherein, $R^1$, $R^2$ and n have the same meanings as described above) or a compound of the formula (IIb):

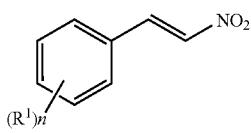

(I)

(wherein, $R^1$ and n have the same meanings as described above)
and a compound of the formula (I'):

CH$_2$(CO$_2$R$^2$)$_2$ (wherein, $R^2$ has the same meaning as described above)
in the presence of an asymmetric catalyst.

5. The method according to claim 4, wherein the reaction of a compound of the formula (I) and a compound of the formula (I') is carried out after dissolving or dispersing a hydrated crystal of a compound of the formula (I) in a solvent, and subjecting the solution or dispersion to liquid-separation, to concentration under reduced, pressure, or to liquid-separation and concentration under reduced pressure.

6. The method according to claim 1, wherein the compound of the formula (IIIa) or the compound of the formula (IIIb) is obtained by reacting a compound of the formula (I) and a compound of the formula (I') in the presence of an asymmetric catalyst, and reducing and cyclizing the resultant compound of the formula (IIa) or compound of the formula (IIb) in the form of solution or dispersion without isolation.

7. The method according to claim 6, wherein the reduction of a compound of the formula (IIa) or a compound of the formula (IIb) is catalytic hydrogen reduction in the presence of a developed nickel containing iron.

8. The method according to claim 6, wherein the reaction of a compound of the formula (I) and a compound of the formula (I') is carried out after dissolving or dispersing a hydrated crystal of a compound of the formula (I) in a solvent, and subjecting the solution or dispersion to liquid-separation, to concentration under reduced pressure, or to liquid-separation and concentration under reduced pressure, and the reduction of a compound of the formula (IIa) or a compound of the formula (IIb) is catalytic hydrogen reduction in the presence of a developed nickel containing iron.

9. The method according to claim 6, wherein the concentration of the compound of the formula (IIa) or the compound of the formula (IIb) is maintained in the range of 10 to 80 wt % from obtaining by the reaction of a compound of the formula (I) and a compound of the formula (I') to reduction and cyclization.

10. The method according to claim 9, wherein the concentration of the compound of the formula (IIa) or the compound of the formula (IIb) is maintained in the range of 20 to 70 wt %.

11. The method according to claim 6, wherein the solvent for the compound of the formula (IIa) or the compound of the formula (IIb) in the form of solution or dispersion is an aromatic hydrocarbon.

12. The method according to claim 6, wherein the reaction of a compound of the formula (I) and a compound of the formula (I') is carried out after dissolving or dispersing a hydrated crystal of a compound of the formula (I) in a solvent, and subjecting the solution or dispersion to liquid-separation, to concentration under reduced pressure, or to liquid-separation and concentration under reduced pressure.

13. The method according to claim 12, wherein the hydrated crystal contains water in an amount of 0.05 to 3 parts by weight with respect to 1 part by weight of the compound of the formula (I).

14. A method comprising catalytic hydrogen reduction and cyclization of a compound of the formula (IIa):

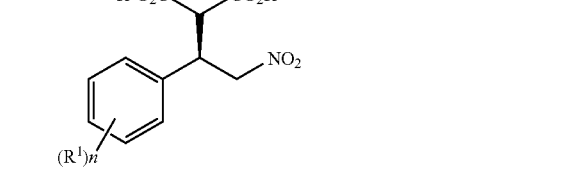

(IIa)

(wherein, n represents an integer of 0 to 3, $R^1$ represents a halogen atom, alkyl group, alkoxy group, haloalkyl group and cycloalkyloxy group, when n is 2 or 3, $R^1$s may be the same or different, or when n is 2 or 3, two $R^1$s together form an alkylenedioxy group, $R^2$ represents an alkyl group) or a compound of the formula (IIb):

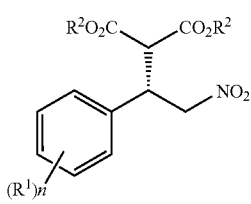

(wherein, $R^1$, $R^2$ and n have the same meanings as described above)
in the presence of a developed nickel containing iron, to produce a compound of the formula (IIIa):

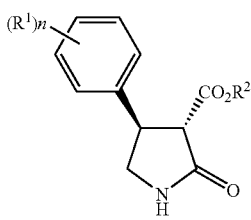

(wherein, $R^1$, $R^2$ and n have the same meanings as described above) or a compound of the formula (IIIb):

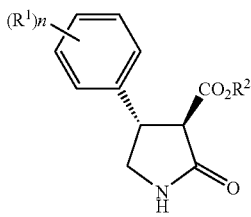

(wherein, $R^1$, $R^2$ and n have the same meanings as described above).

15. The method according to claim 14, wherein the iron content of the developed nickel containing iron is 0.1 to 50 wt %.

16. The method according to claim 14, wherein the compound of the formula (IIa) or the compound of the formula (IIb) is obtained by reaction of a compound of the formula (I):

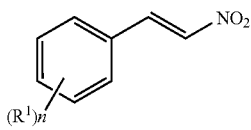

(wherein, $R^1$ and n have the same meanings as described above)
and a compound of the formula (I'):

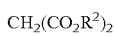

(wherein, $R^2$ has the same meaning as described above)
in the presence of a catalyst, and the catalytic hydrogen reduction in the presence of a developed nickel containing iron is carried out in the form of solution or dispersion of the compound of the formula (IIa) or the compound of the formula (IIb) without isolation.

17. The method according to claim 16, wherein the concentration of the compound of the formula (IIa) or the compound of the formula (IIb) is maintained in the range of 10 to 80 wt % from obtaining by the reaction of a compound of the formula (I) and a compound of the formula (I') to reduction and cyclization.

18. The method according to claim 17, wherein the concentration of the compound of the formula (IIa) or the compound of the formula (IIb) is maintained in the range of 20 to 70 wt %.

19. The method according to claim 16, wherein the solvent for the compound of the formula (IIa) or the compound of the formula (IIb) in the form of solution or dispersion is an aromatic hydrocarbon.

20. The method according to claim 16, wherein the reaction of a compound of the formula (I) and a compound of the formula (I') is carried out after dissolving or dispersing a hydrated crystal of a compound of the formula (I) in a solvent, and subjecting the solution or dispersion to liquid-separation, to concentration under reduced pressure, or to liquid-separation and concentration under reduced pressure.

21. The method according to claim 20, wherein the hydrated crystal contains water in an amount of 0.05 to 3 parts by weight with respect to 1 part by weight of the compound of the formula (I).

22. A method of producing a compound of the formula (Va) or its salt or a compound of the formula (Vb) or its salt, comprising
a step of catalytic hydrogen reduction and cyclization of a compound of the formula (IIa):

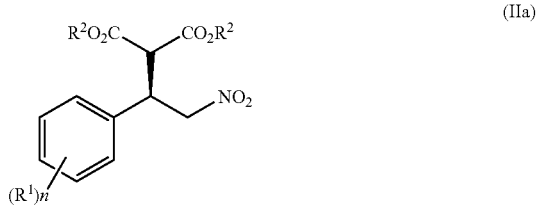

(wherein, n represents an integer of 0 to 3, $R^1$ represents a halogen atom, alkyl group, alkoxy group, haloalkyl group and cycloalkyloxy group, when n is 2 or 3, $R^1$'s may be the same or different, or when n is 2 or 3, two $R^1$'s together form an alkylenedioxy group, $R^2$ represents an alkyl group) or a compound of the formula (IIb):

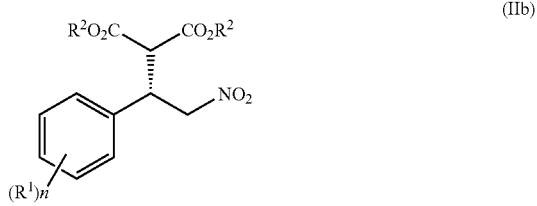

(wherein, $R^1$, $R^2$ and n have the same meanings as described above)

in the presence of a developed nickel containing iron, to produce a compound of the formula (IIIa):

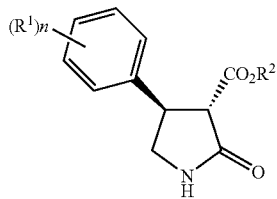
(IIIa)

(wherein, $R^1$, $R^2$ and n have the same meanings as described above) or a compound of the formula (IIIb):

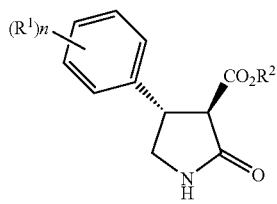
(IIIb)

(wherein, $R^1$, $R^2$ and n have the same meanings as described above);

a step of hydrolysis and decarboxylation of the compound of the formula (IIIa) or the compound of the formula (IIIb), to obtain a compound of the formula (IVa):

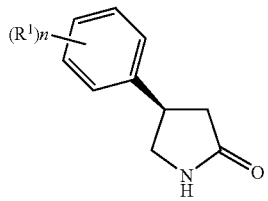
(IVa)

(wherein, $R^1$ and n have the same meanings as described above) or a compound of the formula (IVb):

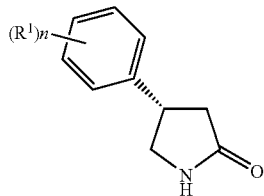
(IVb)

(wherein, $R^1$ and n have the same meanings as described above); and a step of ring-opening the compound of the formula (IVa) or the compound of the formula (IVb), to obtain a compound of the formula (Va):

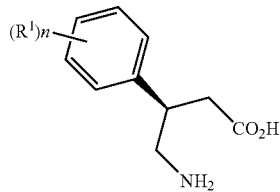
(Va)

(wherein, $R^1$ and n have the same meanings as described above) or its salt or a compound of the formula (Vb):

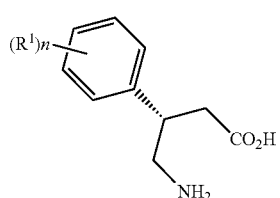
(Vb)

(wherein, $R^1$ and n have the same meanings as described above) or its salt.

23. The method according to claim 22, wherein the iron content of the developed nickel containing iron is 0.1 to 50 wt %.

24. The method according to claim 22, wherein the compound of the formula (IIa) or the compound of the formula (IIb) is obtained by reaction of a compound of the formula (I):

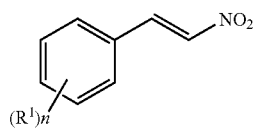
(I)

(wherein, $R^1$ and n have the same meanings as described above)
and a compound of the formula (I'):

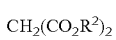

$CH_2(CO_2R^2)_2$ (wherein, $R^2$ has the same meaning as described above)
in the presence of an asymmetric catalyst.

25. The method according to claim 24, wherein the catalytic hydrogen reduction in the presence of a developed nickel containing iron is carried out in the form of solution or dispersion of the compound of the formula (IIa) or the compound of the formula (IIb) without isolation.

26. The method according to claim 25, wherein the concentration of the compound of the formula (IIa) or the compound of the formula (IIb) is maintained in the range of 10 to 80 wt % from obtaining by the reaction of a compound of the formula (I) and a compound of the formula (I') to reduction and cyclization.

27. The method according to claim 26, wherein the concentration of the compound of the formula (IIa) or the compound of the formula (IIb) is maintained in the range of 20 to 70 wt %.

28. The method according to claim 25, wherein the solvent for the compound of the formula (IIa) or the compound of the formula (IIb) in the form of solution or dispersion is an aromatic hydrocarbon.

29. The method according to claim 24, wherein the reaction of a compound of the formula (I) and a compound of the formula (I') is carried out after dissolving or dispersing a hydrated crystal of a compound of the formula (I) in a solvent, and subjecting the solution or dispersion to liquid-separation, to concentration under reduced pressure, or to liquid-separation and concentration under reduced pressure.

30. The method according to claim 29, wherein the hydrated crystal contains water in an amount of 0.05 to 3 parts by weight with respect to 1 part by weight of the compound of the formula (I).

31. A method of producing a compound of the formula (Va) or its salt, comprising
a step of reacting a compound of the formula (I):

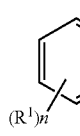

(I)

(wherein, n represents an integer of 0 to 3, $R^1$ represents a halogen atom, alkyl group, alkoxy group, haloalkyl group and cycloalkyloxy group, when n is 2 or 3, $R^1$s may be the same or different, or when n is 2 or 3, two $R^1$s together form an alkylenedioxy group)
with a compound of the formula (I'):

(wherein, $R^2$ represents an alkyl group)
in the presence of nickel(II)bis[(S,S)—N,N'-dibenzylcyclohexane-1,2-diamine]bromide, to obtain a compound of the formula (IIa):

(IIa)

(wherein, $R^1$, $R^2$ and n have the same meanings as described above);
a step of reducing and cyclizing the compound of the formula (IIa) to obtain a compound of the formula (IIIa):

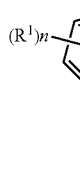

(IIIa)

(wherein, $R^1$, $R^2$ and n have the same meanings as described above); and
a step of dissolving or dispersing the compound of the formula (IIIa) in a solvent, and adding the resultant solution or dispersion to an acid, to obtain a compound of the formula (Va):

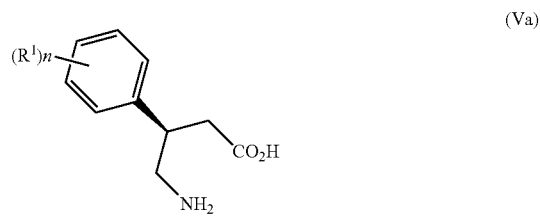

(Va)

(wherein, $R^1$ and n have the same meanings as described above) or its salt.

32. The method according to claim 4, wherein the compound of the formula (I) is produced by reacting a compound of the formula (Ia):

(Ia)

(wherein, $R^1$ and n have the same meanings as described above)
with nitromethane and ammonium acetate in acetic acid.

33. The method according to claim 8, wherein the solvent for dissolving or dispersing a hydrated crystal of a compound of the formula (I) is an aromatic hydrocarbon.

34. The method according to claim 1, wherein n is 1.

35. The method according to claim 34, wherein $R^1$ is situated at the 4-position of a benzene ring.

36. The method according to claim 1, wherein $R^1$ is a halogen atom.

37. The method according to claim 1, wherein n is 1, and $R^1$ is a chlorine atom situated at the 4-position of a benzene ring.

38. The method according to claim 1, wherein the asymmetric catalyst is 1-(3,5-bis(trifluoromethyl)phenyl)-3-((1R,2R)-2-(dimethylamino)cyclohexyl)thiourea, 1-(3,5-bis(trifluoromethyl)phenyl)-3-((1S,2S)-2-(dimethylamino)cyclohexyl)thiourea, nickel(II)bis[(S,S)—N,N'-dibenzylcyclohexane-1,2-diamine]bromide or nickel(II)bis[(R,R)—N,N'-dibenzylcyclohexane-1,2-diamine]bromide.

39. The method according to claim 38, wherein the asymmetric catalyst is nickel(II)bis[(S,S)—N,N'-dibenzylcyclohexane-1,2-diamine]bromide or nickel(II)bis[(R,R)—N,N'-dibenzylcyclohexane-1,2-diamine]bromide.

* * * * *